(12) United States Patent
Yang et al.

(10) Patent No.: US 9,115,082 B2
(45) Date of Patent: Aug. 25, 2015

(54) DIPEPTIDYL-PEPTIDASE-IV INHIBITORS FOR TREATMENT OF TYPE 2 DIABETES COMPLEX WITH HYPERTENSION

(71) Applicants: Catherine Yang, Cherry Hill, NJ (US); Weixing Li, Ellicott City, MD (US)

(72) Inventors: Catherine Yang, Cherry Hill, NJ (US); Weixing Li, Ellicott City, MD (US)

( * ) Notice: Subject to any disclaimer, the term of this patent is extended or adjusted under 35 U.S.C. 154(b) by 0 days.

(21) Appl. No.: 13/744,795

(22) Filed: Jan. 18, 2013

(65) Prior Publication Data

US 2013/0184322 A1 Jul. 18, 2013

Related U.S. Application Data

(60) Provisional application No. 61/587,826, filed on Jan. 18, 2012.

(51) Int. Cl.
*C07D 207/16* (2006.01)
*A61K 31/40* (2006.01)

(52) U.S. Cl.
CPC ............. *C07D 207/16* (2013.01); *A61K 31/40* (2013.01)

(58) Field of Classification Search
CPC .............................. C07D 207/16; A61K 31/40
USPC .......................................... 548/540; 514/423
See application file for complete search history.

(56) References Cited

U.S. PATENT DOCUMENTS

| | | | |
|---|---|---|---|
| 5,543,396 A | 8/1996 | Powers | |
| 6,107,317 A | 8/2000 | Villhauer | |
| 6,166,063 A | 12/2000 | Villhauer | |
| 6,172,081 B1 | 1/2001 | Damon | |
| 2001/0031780 A1 | 10/2001 | Kanstrup | |

FOREIGN PATENT DOCUMENTS

| | | |
|---|---|---|
| DE | 199740832 | 11/1997 |
| EP | 199534538 | 12/1995 |
| EP | 199819998 | 5/1998 |
| GB | 199515309 | 6/1995 |
| WO | 9403055 | 2/1994 |
| WO | 9511689 | 5/1995 |
| WO | 0134594 | 5/2001 |
| WO | 0168603 | 9/2001 |

OTHER PUBLICATIONS

Demuth et al. (CAPLUS abstract of: WO 2001/072290) (2010).*
Niedermeyer et al., Eur. J. Biochem. 1998 254 (1998):650-4.
Tang et al., Proc. Natl. Acad. Sci. U.S.A. 97 (2000) 6025-6030.
Augustyns et al., Current Medicinal Chemistry, 6 (1999) 311-327.
Duke-Cohan et al., J. Immunol. 156 (1996) 1714-1721.
Wilson et al., J Androl. 21 (2000) 220-226.
Fric et al., Eur. J. Cancer Prey. 9 (2000):265-268.
Van Den Oord, Br. J. Dermatol. 138 (1998) 615-621.
Sedo et al., J Cancer Res. Clin. Oncol. 117 (1991) 249-253.
Minelli et al., J Reprod. Fertil. 114 (1998) 237-243.
Agrawal et al., J Reprod. Fertil.79 (1987) 409-419.
Arienti et al., FEBS Lett.410 (1997) 343-346.
Raynaud et al., J Cell Physiol. 151 (1992) 378.
Augustyns et al., Curr. Med. Chem.6 (1999) 311-327.
Hildebrandt et al., Clinical Science 99 (2000) 93-104.
Rosenstock et al, "Dipeptidyl peptidase-4 inhibitors and the management of type 2 diabetes mellitus", Curr Opin Endocrinol Diabetes Obes 14 (2): 98-107 (Apr. 2007).

* cited by examiner

*Primary Examiner* — Robert Havlin
(74) *Attorney, Agent, or Firm* — Ober, Kaler, Grimes & Shriver

(57) ABSTRACT

The invention comprises novel inhibitors of dipeptidyl peptidase IV (DPP-IV) with beta blocker activity, pharmaceutical compositions comprising therapeutically effective amounts of novel inhibitors of DPP-IV, and novel methods of treating medical conditions are provided. The novel inhibitors of DPP-IV described herein are useful in the treatment of neurological disorders, diabetes, inflammatory disorders such as arthritis, obesity, osteoporosis, hypertension, and glaucoma of such other enumerated conditions as can be treated with inhibitors of DPP-IV and beta blockers.

2 Claims, 2 Drawing Sheets

| Structures | Compound | IC$_{50}$ (nM) |
|---|---|---|
| 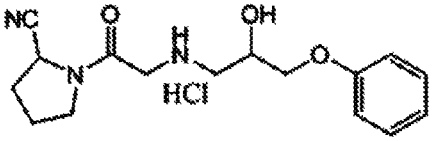 | 7 | 1.5 |
| 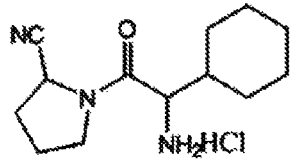 | 8 | 46 |
| 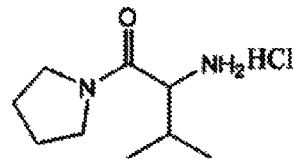 | 9 | 548 |
| 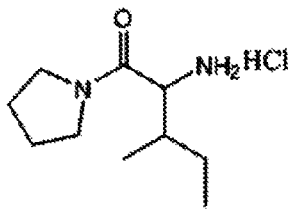 | 10 | 2000 |
| 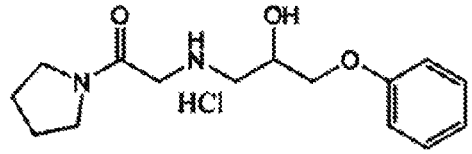 | 11 | 12000 |
| 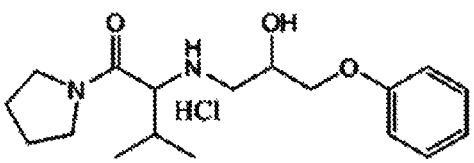 | 12 | 8500 |
| 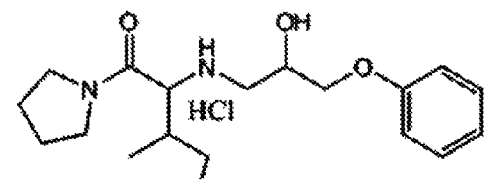 | 13 | 33000 |
FIG. 2
|  | IC50 (μM) | Ki |
|---|---|---|
| adrenergic β$_1$: | 17 | 9.83 |
| adrenergic β$_2$: | 32 | 22 |
FIG. 3

DIPEPTIDYL-PEPTIDASE-IV INHIBITORS FOR TREATMENT OF TYPE 2 DIABETES COMPLEX WITH HYPERTENSION

CROSS-REFERENCE TO RELATED APPLICATION(S)

The present application derives priority from U.S. provisional application Ser. No. 61/587,826 filed Jan. 18, 2012 which is incorporated herein by reference.

BACKGROUND OF THE INVENTION

1. Field of the Invention

The present invention relates to new and improved inhibitors of Dipeptidyl-Peptidase-IV (DPP-IV) with beta blocker activity, and new and improved treatment methods and related uses. The inhibitors according to the invention are useful for treating and detecting a wide variety of diseases and other abnormal conditions, including diseases impacting the central nervous system.

2. Description of the Background

Dipeptidyl-peptidase-IV (DPP-IV, EC 3.4.14.5) is a protein that, in humans, is encoded by the DPP4 gene. The protein is an antigenic enzyme expressed on the surface of most cell types and is associated with immune regulation, signal transduction and apoptosis. More specifically it is a membrane-anchored aminopeptidase involved in the release of N-terminal dipeptides from proteins and other types or forms of peptides. The enzyme is a type II membrane serine peptidase, and has a substrate preference for proteins or peptides which carry a proline at the penultimate position of their N-termini. The peptide bonds before and after a proline residue is relatively resistant to cleavage by common proteases. It has been speculated that the presence of proline at the penultimate position of the peptide chain—a feature shared by a number of immunopeptides, neuropeptides, and peptide hormones—protects such peptides from degradation by unspecific exopeptidases. A physiological role for DPP-IV would be in the activation, inactivation, or degradation of its substrates through the specific release of a proline-containing dipeptide from the N-terminal region of the substrate peptide.

DPP-IV has been found in the kidney, epithelial cells, endothelial cells, small intestine, prostate, brain, placenta, and liver. In T-cells, it has been shown to be identical to the memory cell surface antigen CD26. Other proteins which display DPP-IV-like activity include fibroblast-activation protein (FAP), an inducible type-II cell-surface glycoprotein selectively expressed by reactive stromal fibroblasts of epithelial cancers and healing wounds [Niedermeyer, et al., Eur. J. Biochem. 1998 254 (1998):650-4] and attractin/mahogany protein, which exists in membrane-bound and secreted forms and is implicated in control of pigmentation, energy metabolism, and CNS myelination [Tang et al., Proc. Natl. Acad. Sci. U.S.A. 97 (2000) 6025-30.].

DPP-IV activity has also been found in serum, urine, seminal plasma, and amniotic fluid. It has been speculated that this soluble DPP-IV activity can be attributed to cleavage of the membrane-bound form of DPP-IV and release of its catalytic portion into the bloodstream [Augustyns, K., et al., Current Medicinal Chemistry, 6 (1999) 311-327]. Additionally, a distinct form of DPP-IV, which appears to be a breakdown product of the T-cell surface antigen DPPT-L, has been described in human plasma. [Duke-Cohan, et al., J. Immunol. 156 (1996) 1714-21].

The physiological roles of DPP-IV have not been completely elucidated. It has been thought that DPP-IV plays a role, amongst others, in the regulation of fat intake, natriuresis, nociception, T-cell activation, regulation of blood glucose, and regulation of the digestive tract. DPP-IV has been implicated in disease states such as HIV infection, diabetes, arthritis and certain cancers. For example, DPP-IV activity and/or expression was found to be elevated in prostate [Wilson, et al., J Androl. 21 (2000) 220-6], colon [Fric, et al., Eur. J. Cancer Prev. 9 (2000):265-8], skin [Van den Oord, Br. J. Dermatol. 138 (1998) 615-21] and lung cancer [Sedo, et al., J Cancer Res. Clin. Oncol. 117 (1991) 249-53], and elevated DPP-IV also has been found in patients having benign prostate hyperplasia. A high activity of DPP-IV is also associated with membrane vesicles found in human, bovine, and equine ejaculate, where it is thought to play a role in the regulation of sperm motility and viability [Minelli A, et al., J Reprod. Fertil. 114 (1998) 237-43; Agrawal, et al., J Reprod. Fertil. 79 (1987) 409-19; Arienti, et al., FEBS Lett. 410 (1997) 343-6].

DPP-IV also is being investigated for its role in type II diabetes because the glucagon-like peptide (GLP-1) can be a substrate for DPP-IV cleavage, and some DPP-IV inhibitors have demonstrated efficacy in animal models of diabetes. Additionally, DPP-IV has been implicated in HIV infection due to its association with CD 26.

High levels of DPP-IV expression have been reported for skin fibroblasts from human patients suffering from psoriasis, rheumatoid arthritis, and lichen planus [Raynaud, et al., J Cell Physiol. 151 (1992) 378]. Inhibition of DPP-IV has been shown to increase release of TGF-beta, a protein having neuroprotective properties. DPP-IV inhibition itself has been implicated in cellular mechanisms relating to neurodegeneration [see PCT publication WO 01/34594].

It follows from the above that inhibitors of DPP-IV may be useful as pharmaceuticals in the treatment of a range of medical conditions. In particular, they may be useful as immunosuppressants, anti-inflammatory agents, drugs that suppress tumor invasion and metastasis formation, drugs that inhibit HIV infectivity, regulators of blood glucose levels in patients suffering from diabetes, agents that affect sperm motility and viability useful both for contraception and in the reproduction of livestock, drugs for the treatment of dermatological disorders such as psoriasis, and as pharmaceuticals for the treatment of neurological disorder.

DPP-IV inhibition has been studied in the treatment of autoimmune diseases such as diabetes, arthritis and multiple sclerosis. See PCT publications WO 97/40832 and WO 98/19998. Additionally, PCT publication WO 94/03055 discusses increasing production of hematopoietic cells with DPP-IV inhibitors. PCT publication WO 95/11689 discloses the use of DPP IV inhibitors to block the entry of HIV into cells. U.S. Pat. No. 5,543,396 discloses the use of inhibitors (certain prolinephosphonate derivatives) to treat tumor invasion. PCT publication WO 95/34538 mentions the use of certain serine protease inhibitors (such as certain DPP-IV and PEP inhibitors) to treat inflammation-related neurological/autoimmune diseases like multiple sclerosis. Efficacy in experimental models of inflammatory disorders has also been described for compounds with DPP-IV inhibitory activity, suggesting that such compounds may be useful in the treatment of medical conditions such as rheumatoid arthritis and inflammatory bowel disorder. Augustyns et al. (Curr. Med. Chem. 6 (1999) 311-327) and Hildebrandt et al. (Clinical Science 99 (2000) 93-104) review the wide therapeutic potential of various classes of DPP-IV inhibitors. Oral DPP-IV inhibitors have been found to improve glucose-dependent insulin secretion and reduce inappropriate glucagon secretion. [Rosenstock et al, "Dipeptidyl peptidase-4 inhibitors and the management of type 2 diabetes mellitus", Curr Opin Endocrinol Diabetes Obes 14 (2): 98-107 (April 2007)].

DPP-IV inhibitors based upon molecules that bear a resemblance to proline have been investigated in the field. For example, PCT publication WO 95/11689 discloses alpha-amino boronic acid analogs of proline. PCT publication WO 98/19998 discloses N-substituted 2-cyanopyrrolidines as DPP-IV inhibitors. PCT publication WO 95/34538 discloses various proline containing compounds and phosphonate derivatives thereof. Prolinephosphonate derivatives as inhibitors of DPP-IV are also disclosed in U.S. Pat. No. 5,543,396. U.S. Pat. No. 6,172,081 discloses a series of tetrahydroisoquinoline 3-carboxaminde derivatives with potent DPP-W inhibitory activity; U.S. Pat. Nos. 6,166,063 and 6,107,317 disclose N-substituted 2-cyanopyrrolidines and 4-cyanothiazolidines, respectively. WO 95/15309 discloses various aminoacyl compounds as inhibitors of DPP-IV. WO 01/68603 discloses a class of cyclopropyl-fused pyrrolidine derivatives as inhibitors of DPP-IV. N-substituted 2-cyanopyrrole derivatives as inhibitors of DPP-IV, and pharmaceutical compositions thereof, are taught for the treatment of various metabolic disorders in U.S. Patent Application Publication 2001/0031780.

Beta blockers (sometimes written as β-blockers) or beta-adrenergic blocking agents, beta-adrenergic antagonists, beta-adrenoreceptor antagonists or beta antagonists, are a class of drugs used for various indications. They are particularly for the management of cardiac arrhythmias, cardioprotection after myocardial infarction (heart attack), and hypertension. As beta adrenergic receptor antagonists, they diminish the effects of epinephrine (adrenaline) and other stress hormones. In 1958 the first beta blocker, dichloroisoproterenol, was synthesized by Eli Lilly Laboratories, but it was Sir James W. Black in 1962, who found the first clinically significant use of beta blockers with propranolol and pronethalol; it revolutionized the medical management of angina pectoris and is considered by many to be one of the most important contributions to clinical medicine and pharmacology of the 20th century.

SUMMARY OF THE INVENTION

It is, therefore, an object of the present invention to provide new therapeutic products, methodologies, and novel inhibitors of dipetidyl peptidase, additionally having other activities such as beta blocking activity. In accomplishing this object and other objects, there are provided, in accordance with one aspect of the invention, inhibitors of dipeptidyl peptidase IV which comprise modified N-substituted cyanopyrrolidine compounds of the general formulas described below in detail.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 2 is a Table of exemplary DppIV Inhibitors according to the present invention with their IC50 values.

FIG. 3 is a Table of the results of an adrenergic $\beta_1$ assay and adrenergic $\beta_2$ assay for compound (7) of FIG. 2.

DETAILED DESCRIPTION OF THE INVENTION

Figure 1:
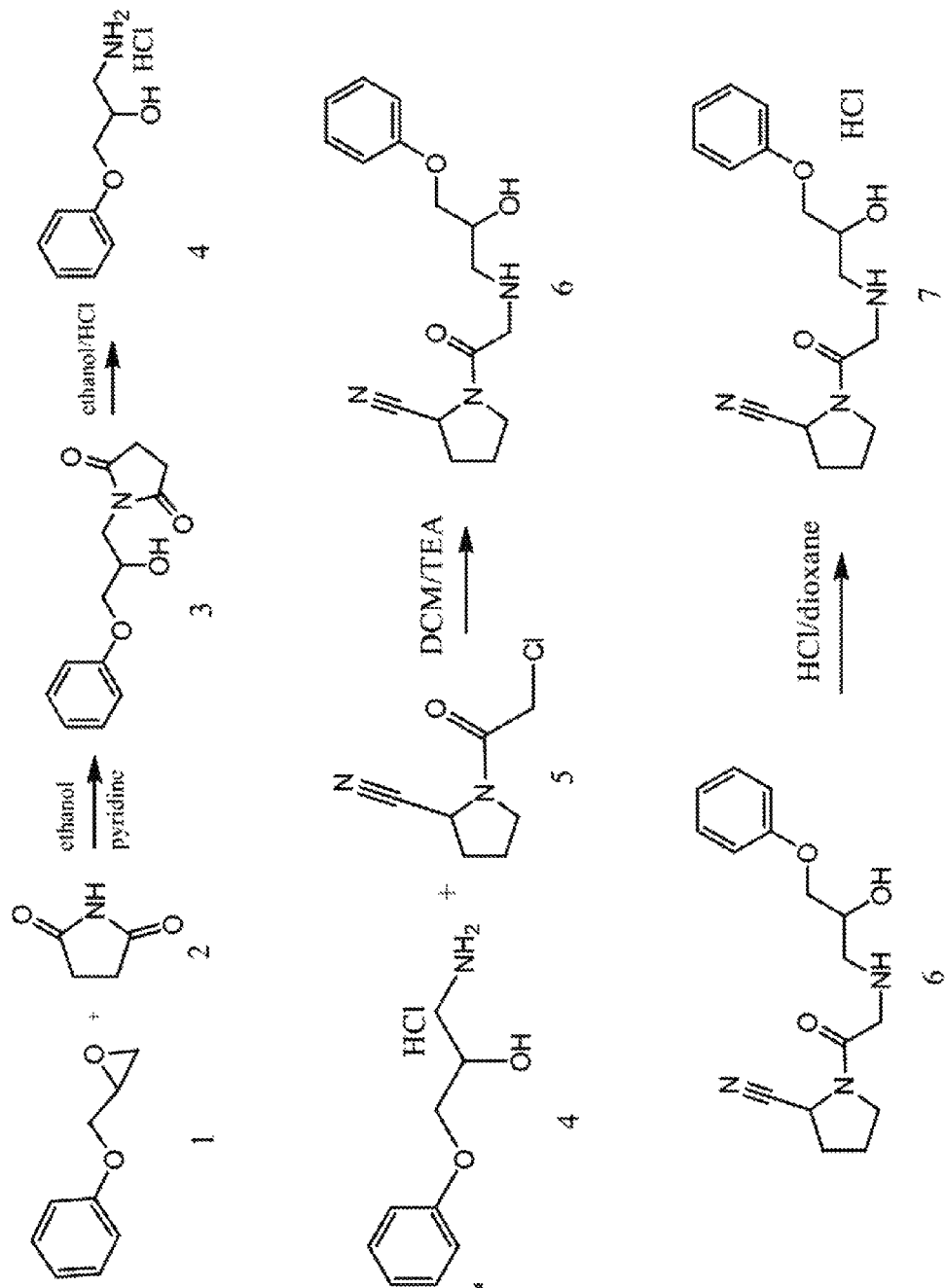
FIG. 1 is a an exemplary synthetic sequence for producing 1-(2-(2-hydroxy-3-phenoxypropylamino)acetyl)pyrrolidine-2-carbonitrile hydrochloride according to an embodiment of the invention.

The present invention provides novel inhibitors of dipeptidyl peptidase IV with other activities such as beta blocker activity, which include modified N-substituted pyrrolidine compounds of the following general formula I (1)

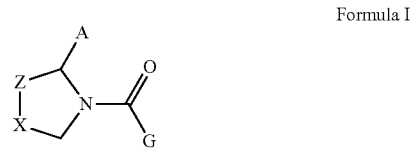

Formula I wherein the pyrrolidine ring formed by X, Z, N, and the carbon atoms to which they are attached, is saturated, or optionally contains one double bond;

A may be H, F or CN;

X is selected from the group consisting of $CH_2$, CH, S, O, NH, N, C=O, $CF_2$, CF, CH—Y, and C—Y; wherein Y is a halogen, hydroxy, or C1-C3 alkyloxy;

Z is selected from the group consisting of $CH_2$, CH, $CF_2$, CF, C—Y and CH—Y;

wherein one of X or Z must be $CH_2$; or CH if said pyrrolidine ring contains one double bond; and where G is

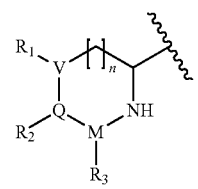

wherein M, Q, and V represent carbon atoms;

n is 0 or 1; and where either $R_1$ and $R_2$, taken together with V and Q, or $R_2$ and $R_3$, taken together with Q and M, form a 3-6 membered, saturated carbocyclic or heterocyclic ring which may contain one or two heteroatoms selected from the group consisting of O, S, and N.

In another aspect of this invention, there are provided inhibitors of DPP IV of the following general Formula II and IIa:

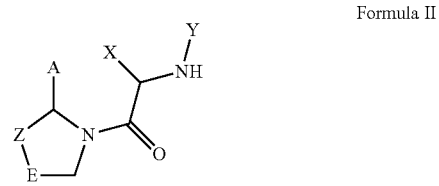

Formula II

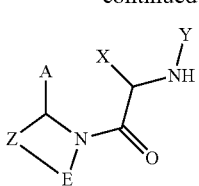

Formula IIa where A may be H, F or CN;

where X and Y may independently be H, or W, W' or W", wherein W' is a saturated cyclic hydrocarbon; and W" is a non-cyclic straight or branched chain alkyl group; and W may be a group defined by Formula III or VI.

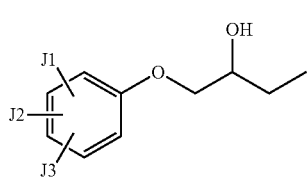

Formula III

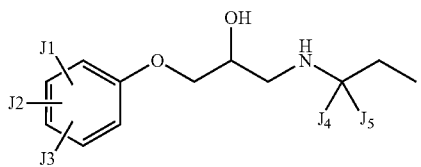

Formula IV where J1 is any one of:
(1) hydrogen,
(2) hydroxy,
(3) hydroxymethyl; or
(4) alkyl, aryl, alkoxy, aroxy; and
J2 and J3 are independently any one of
(1) hydrogen,
(2) halo such as chloro, bromo or fluoro,
(3) hydroxy,
(4) amino,
(5) di(C1-5 alkyl)amino,
(6) mono(C1-5 alkyl)amino,
(7) nitro,
(8) cyano,
(9) C1-6 alkyl,
(10) C3-8 cycloalkyl,
(11) C2-5 alkenyl,
(12) C1-4 alkoxy,
(13) C1-4 alkylthio,
(14) C2-5 alkenyloxy,
(15) C1-5 alkanoyl, such as formyl, pentanoyl or the like.
(16) alkyl, aryl, alkoxy, aroxy, or
(17) heterocyclic.
J1 and J2 or J2 and J3 may form a cyclic ring, aliphatic or aromatic ring.
J4, J5 may be H, F, Cl, alkyl, aryl, heterocycle groups.

The novel compounds of this invention include all the optical isomer forms as pure enantiomers or as mixtures containing the optical isomers such as racemic mixtures and compounds. The novel compounds of this invention include all the salt forms as pure salts or mixtures containing them. The salt may be formed between the novel compounds and hydrochloric acid, acetic acid, formic acid, citric acid, fumaric acid, tartaric acid, succinic acid. The novel Dipeptidyl-Peptidase-IV "Inhibitors" according to the present invention show an inhibitory effect on the DppIV measured as IC50 within a range of from 0.0015 uM to 33 uM. The inhibitory effect on DppIV can be determined by methods known in the literature. The procedure for IC50 is described below and in regard to FIG. 2.

The proteolytic enzyme, Dipeptidyle Peptidase IV (DppIV) was monitored in vitro by the substrate Gly-Pro 4-methoxy-β-naphthylamide while in the presence of compound 7. 20 ul of 1.3 mM DppIV was pipetted into twenty-four micro centrifuge tubes containing various concentrations of compound 7 in a total volume of 100 uL. The samples were thoroughly vortexed and centrifuged at 5,000 RPM for 30 seconds. The micro centrifuge tube were then placed in a 37° C. water bath and incubated for 30 minutes. After incubation, 0.625 uM of substrate was added and the volume was adjusted to 130 uM with incubation buffer. Samples were thoroughly mixed and centrifuged at 5,000 RPM for 30 seconds before placed in a 37° C. water bath for an additional 30 minutes. The reaction was terminated by adding 1 ml of 100 mM Citrate buffer pH 4.0 and vortexing thoroughly for 1 minute. The excitation and emission spectrum of each sample was measured at 340 nm and 425 nm respectfully on a Fluoromax-II Fluorometer. Blanks for each sample were prepared by adding citrate buffer prior to starting the reaction with substrate.

FIG. 2 is a Table of exemplary DppIV Inhibitors according to the present invention with their IC50 values, including 1-(2-(2-hydroxy-3-phenoxypropylamino)acetyl)pyrrolidine-2-carbonitrile hydrochloride (as shown below in FIG. 1 at 7). The IC50 values of 1-(2-(2-hydroxy-3-phenoxypropylamino)acetyl)pyrrolidine-2-carbonitrile hydrochloride (FIG. 1 compound were also measured in an adrenergic $\beta_1$ assay and adrenergic $\beta_2$ assay. The results of the adrenergic $\beta_1$ assay and adrenergic $\beta_2$ assay are shown in FIG. 3, and the procedures are described below.

Procedure for Adrenergic $\beta_1$ Assay:

Human recombinant adrenergic $\beta_1$ receptors expressed in CHO-K1 cells are used in modified Tris-HCl buffer pH 7.4. A 25 µg aliquot is incubated with 0.03 nM [$^{125}$I]Cyanopindolol for 120 minutes at 25° C. Non-specific binding is estimated in the presence of 100 µM S(−)-Propranolol. Receptors are filtered and washed, the filters are then counted to determine [$^{125}$I]Cyanopindolol specifically bound. Compounds are screened at 10 µM.

Procedure for Adrenergic $\beta_2$ Assay:

Human recombinant adrenergic $\beta_2$ receptors expressed in CHO cells are used in modified Tris-HCl buffer pH 7.4. A 50 µg aliquot is incubated with 0.2 nM [$^3$H]CGP-12177 for 60 minutes at 25° C. Non-specific binding is estimated in the presence of 10 µM ICI-118551. Receptors are filtered and washed, the filters are then counted to determine [$^3$H]CGP-12177 specifically bound. Compounds are screened at 10 µM.

The compounds of Formulae I, II and IIa possess important utility as pharmaceuticals, especially in the treatment of medical conditions which can be alleviated by inhibition of DppIV. Examples of such medical conditions are recited below. However, the methods of the present invention are not limited to the treatment of such medical conditions alone. Thus, the ability of the compounds of the instant invention to bind to, and inhibit DppIV further renders the compounds of Formulae I, II and IIa useful in a variety of diagnostic and research applications. For example, in vitro techniques can be used to identify and characterize cellular components or chemical compounds that interact with DppIV in a cell-free environment, as would be the case when a compound of Formulae I, II or IIa is used to competitively bind to, or inhibit, DppIV in the presence of such other chemical compound or cellular component. Further, compounds of Formulae I, II and IIa may be labeled with a suitable radioisotope and in such form utilized for determining the cellular or tissue distribution of DppIV in a given tissue sample, or utilized as a diagnostic medical imaging agent for the visualization of e.g. tumors which express high levels of DppIV.

Another aspect of this invention provides methods for treating a medical condition in a patient in need of such treatment. Medical conditions to be treated with the compounds and compositions of this invention according to these methods include neurological disorders, diabetes, hyperglycemnia, obesity, atherosclerosis, polycystic ovary syndrome, arthritis, autoimmune disorders, AIDS, osteoporosis, chronic inflammatory bowel disease, AIDS, metastatic cancer, and cutaneous disorders such as psoriasis and lichen planus. The instant compounds are further useful as immunosuppressants in allograft recipients, contraceptive agents affecting sperm function, and for the treatment of anorexia.

A compound of this invention can be administered to an animal or human patient by itself or in pharmaceutical compositions where it is mixed with suitable carriers or excipients, at doses to treat or ameliorate various conditions. The compounds according to the present invention preferably have sufficient stability, potency, selectivity, solubility and availability to be safe and effective in treating diseases, injuries and other abnormal medical conditions or insults, including medical conditions of, and insults to, the central nervous system, the peripheral nerves, and other organs. A therapeutically effective dose refers to that amount of the compound sufficient to affect an activity in a nerve or neuronal cell, to produce a detectable change in a cell or organism, or to treat a disorder in a human or other mammal. The word "treat" in its various grammatical forms as used in relation to the present invention refers to preventing, curing, reversing, attenuating, alleviating, minimizing, suppressing, ameliorating or halting the deleterious effects of a disease state, disease progression, injury, wound, ischemia, disease causative agent (e.g., bacteria, protozoans, parasites, fungi, viruses, viroids and/or prions), surgical procedure or other abnormal or detrimental condition (all of which are collectively referred to as "disorders," as will be appreciated by the person of skill in the art). A "therapeutically effective amount" of a compound according to the invention is an amount that can achieve effective treatment, and such amounts can be determined in accordance with the present teachings by one skilled in the art.

The methods of the present invention comprise (i.) administration of a compound of Formulae I, II or IIa, where the compound is itself therapeutically active in the treatment of the targeted medical condition, or (ii.) administration of a prodrug of a compound of Formulae I, II or IIa, wherein such prodrug is any compound which is capable of undergoing metabolic conversion to a compound of Formulae I, II or IIa following administration, or (iii.) administration of a compound of Formulae I, II or IIa where the compound is capable of undergoing metabolic conversion to a metabolite following administration, and where the metabolite is therapeutically active in the treatment of the targeted medical condition, or (iv.) administration of a metabolite of a compound of Formulae I, II or IIa, where the metabolite is therapeutically active in the treatment of the targeted medical condition. Thus, the use of a compound of Formulae I, II or IIa in the methods of the present invention explicitly includes not only the use of the compound itself, but also the modifications ii, iii, and iv discussed in this paragraph, and all such modifications are explicitly intended to be within the scope of the following claims.

Therapeutically effective doses may be administered alone or as adjunctive therapy in combination with other treatments. Techniques for the formulation and administration of the compounds of the instant application may, for example, be found in *Remington's Pharmaceutical Sciences*, Mack Publishing Co., Easton, Pa., 18th edition (1990), and subsequent editions thereof.

Suitable routes of administration may, for example, include oral, rectal, transmucosal, buccal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome coated with an antibody. The liposomes will be targeted to and taken up selectively by cells expressing the appropriate antigen.

The pharmaceutical compositions of the present invention may be manufactured in a manner that is itself known, e.g., by means of conventional mixing, dissolving, emulsifying, encapsulating, entrapping, or lyophilizing processes. The following example process is described in regard to FIG. 1:

To obtain 1-(2-hydroxy-3-phenoxypropyl)pyrrolidine-2,5-dione (as shown at 3):

3 drops of pyridine was added to a mixture of 2-(phenoxymethyl)oxirane (4.5 g, 30 mmol) and pyrrolidine-2,5-dione (3.3 g, 33 mmol) in ethanol (35 mL). The reaction mixture was heated to reflux for four hours. After standing at room temperature for 24 hours, a precipitate was obtained (3.7 g). The solid (as shown at 3) 1-(2-dihydroxy-3-phenoxypropyl)pyrrolidine-2,5-dione was collected via filtration and was used in next step without purification. To obtain 1-amino-3-phenoxypropan-2-ol hydrochloride (as shown at 4):

A solution of 1-(2-hydroxy-3-phenoxypropyl)pyrrolidine-2,5-dione (3.5 g, 13.1 mmol) (as shown at 3 above) in HCl (12N, 20 mL) and ethanol (20 mL) was heated to reflux for 6 hours. After thin layer chromatography (TLC) showed the reaction was complete, the mixture was concentrated in vacuum to give a white residue, which was taken up in water (20 mL) and washed with ether (3*50 mL). The aqueous phase was concentrated to give crude product, which was crystallized from methanol to give 2.9 g of 1-amino-3-phenoxypropan-2-ol hydrochloride (as shown at 4).

To obtain 1-(2-(2-hydroxy-3-phenoxypropylamino)acetyl) pyrrolidine-2-carbonitrile (as shown at 6):

A solution of 1-amino-3-phenoxypropan-2-ol hydrochloride (7.9 g, 38.8 mmol) and 1-(2-chloroacetyl)pyrrolidine-2-carbonitrile (6.1 g, 35.3 mmol) in DCM (250 mL) was added triethylamine (15 mL, 106 mmol). The mixture was stirred at room temperature overnight. After the TLC showed that the reaction was complete, the mixture was washed by brine. The aqueous solution was extracted with dichloromethane (DCM) (3×100 mL) and the combined DCM solution was concentrated to give a crude product, which was purified by column chromatography to give 3.5 g of 1-(2-(2-hydroxy-3-phenoxypropylamino)acetyl)pyrrolidine-2-carbonitrile (as shown at 6). Yield was 33.6%.

To obtain 1-(2-(2-hydroxy-3-phenoxypropylamino)acetyl) pyrrolidine-2-carbonitrile hydrochloride (as shown at 7):

1-(2-(2-hydroxy-3-phenoxypropylamino)acetyl)pyrrolidine-2-carbonitrile (3.4 g, 11 mmol) was dissolved in ether (10 mL). Then a solution of HCl in dioxane (4M, 3 mL, 12 mmol) was added to the reaction mixture at −20° C., which was warmed to room temperature and stirred for 1 hour.

After TLC showed that the reaction was complete, the mixture was concentrated. Ether was added to the residue to give 3.5 g of an off-white solid of 1-(2-(2-hydroxy-3-phenoxypropylamino)acetyl)pyrrolidine-2-carbonitrile hydrochloride (as shown at 7). The yield was 89.3%. The molecular weight was confirmed by mass spectroscopy (MS+: 340).

One skilled in the art will readily understand that pharmaceutical compositions for use in accordance with the present invention thus may be formulated in conventional manner using one or more physiologically acceptable carriers comprising excipients and auxiliaries, which facilitate processing of the active compounds into preparations, which can thus be used pharmaceutically.

For injection, the compounds of the invention may be formulated in aqueous solutions, preferably in physiologically compatible buffers, such as Hank's solution, Ringer's solution, or physiological saline buffer. For transmucosal or buccal administration, penetrants appropriate to the barrier to be permeated may be used in the formulation. Such penetrants are known in the art.

For oral administration, the compounds can be formulated readily by combining the active compounds with pharmaceutically acceptable carriers, well known to those in the art. Such carriers enable the compounds of the invention to be formulated as tablets, pills, capsules, liquids, quick dissolving preparations, gels, syrups, slurries, suspensions and the like, for oral ingestion by a patient to be treated. Pharmaceutical preparations for oral use of the compounds of this invention can be obtained by employing a solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In general, the pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. If desired, disintegrating agents may be added, such as the cross-linked polyvinyl pyrrolidone, agar, or alginic acid or a salt thereof such as sodium alginate or a number of others disintegrants (see, for example, *Remington's Pharmaceutical Sciences*, Mack Publishing Co., Easton, Pa., 18th edition (1990), and subsequent editions thereof).

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluorome thane, dichlorotetrafluoroethane, carbon dioxide, pressurized air, or other suitable gas or mixture. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active ingredient may be in powder form for reconstitution with a suitable vehicle, e.g., sterile pyrogen-free water, before use.

The compounds may also be formulated in rectal compositions such as suppositories, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds of the invention may further be formulated in pharmaceutical or cosmetic compositions for topical application to the skin in the form of an aqueous, alcoholic, aqueous/alcoholic or oily solution, or of a dispersion of the lotion or serum type, of an emulsion having a liquid or semi-liquid consistency of the milk type, obtained by dispersion of a fatty phase in an aqueous phase (O/W) or vice versa (W/O), or of a suspension or of an emulsion with a soft consistency of the aqueous or anhydrous gel, foam or cream type, or, alternatively, of microcapsules or microparticles, or of a vesicular dispersion of ionic and/or nonionic type, or may further be administered in the form of an aerosol composition comprising a pressurized propellant agent. The compounds of the invention, for use in the treatment of a cutaneous disorder such as, for example, psoriasis or lichen planus, can also be formulated into various compositions for hair care and, in particular, shampoos, hair-setting lotions, treating lotions, styling creams or gels, dye compositions (in particular oxidation dyes), optionally in the form of color-enhancing shampoos, hair restructuring lotions, permanent-wave compositions, and the like. Pharmaceutical or cosmetic compositions comprising compounds of the invention can also contain additives and adjuvants which are conventional in the cosmetics field, such as gelling agents, preservatives, antioxidants, solvents, fragrances, fillers, screening agents, odor absorbers and colorants. The amounts of these different additives and adjuvants are those typically employed in the cosmetics field and range, for example, from 0.01% to 20% of the total weight of the composition, preferably 0.1% to 10%, and more preferably 0.5% to 5%. In addition to one or several compounds of the invention, compositions for topical application may further contain additional agents already known in the art to promote hair growth or to prevent or retard hair loss, such as, without limitation, tocopherol nicotinate, benzyl nicotinate or 2,4-diamino-6-piperidinopyrimidine 3-oxide, or may contain other active agents such as antibacterial agents, antiparasitic agents, antifungal agents, antiviral agents, anti-inflammatory agents, antipruriginous agents, anaesthetic agents, keratolytic agents, antiseborrhoeic agents, antidandruff agents, or antiacne agents. The cosmetic or pharmaceutical compositions according to the invention can be topically applied onto the affected areas of the scalp and skin of an individual and optionally maintained in contact for a number of hours and optionally rinsed. It is possible, for example, to apply the composition containing an effective amount of at least one compound of the invention in the evening, to retain the composition in contact overnight and optionally to shampoo in the morning. These applications can be repeated daily for one or a number of months, depending on the particular individuals involved.

Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

Pharmaceutical compositions suitable for use in the present invention include compositions wherein the active ingredients are contained in an effective amount to achieve their intended purpose, to effect a therapeutic benefit, or to effect a detectable change in the function of a cell, tissue, or organ. More specifically, a therapeutically effective amount means an amount effective to prevent the development of or to alleviate the existing symptoms of the subject being treated. Determining the effective amount is well within the capability of those skilled in the art, especially in light of the detailed disclosure provided herein.

The compounds of this invention may be administered in conjunction with, or formulated in pharmaceutical compositions together with, one or several additional therapeutic agents. Such additional therapeutic agents are themselves known in the art, and the specific agent employed together with the compounds of Formulae I, II or IIa in this embodiment of the invention depend on the medical condition to be treated. Medical conditions wherein the compounds of Formulae I, II or IIa are useful as therapeutic agents include diabetes, hyperglycemia, impaired glucose homeostasis, impaired glucose tolerance, infertility, polycystic ovary syndrome, growth disorders, frailty, arthritis, allograft rejection in transplantation, autoimmune diseases (such as scleroderma and multiple sclerosis), various immunomodulatory diseases (such as lupus erythematosis or psoriasis), AIDS, intestinal diseases (such as necrotizing enteritis, microvillus inclusion disease or celiac disease), chemotherapy-induced intestinal mucosal atrophy or injury, osteoporosis, Syndrome X dysmetabolic syndrome, diabetic complications, hyperinsulinemia, obesity, atherosclerosis and related diseases, as well as inflammatory bowel disease (such as Crohn's disease and ulcerative colitis), obesity, atherosclerosis, and neurodegenerative disorders.

The instant compounds are further useful as immunosuppressants in allograft recipients, contraceptive agents affecting sperm function, and for the treatment of anorexia It follows that additional therapeutic agents to be used in combination with the compounds of this invention are selected from such agents known in the art to possess therapeutic utility in the medical condition to be treated, In the treatment of diabetes, for example, compounds of Formulae I-XI may be used in combination with one or more other types of antidiabetic agents which may be administered by any of the herein described routes in the same dosage form, or in a separate dosage form. Such other types of antidiabetic agents which may be used in combination with the compounds of this invention are themselves known in the art, and include, for example, biguanides, sulfonyl ureas such as glyburide, glucosidase inhibitors, thiazolidinediones such as troglitazone (Rezulin®), glycogen phosphorylase inhibitors, and insulin. In the treatment of inflammatory disorders, for example, compounds of Formulae I, II and IIa may be used in combination with one or several agents which themselves have therapeutic utility in that condition, such as aspirin, indomethacin, ibuprofen, ketoprofen, naproxen sodium, celecoxib (Celebrex®), or rofexocib (Vioxx®).

Toxicity and therapeutic efficacy of the compounds or compositions can be determined by standard pharmaceutical, pharmacological, and toxicological procedures in cell cultures or experimental animals. For example, numerous methods for determining the LD50 (the dose lethal to 50% of the population) and the ED 50 (the dose therapeutically effective in 50% of the population) exist. The dose ratio between toxic and therapeutic effects is the therapeutic index, which can be expressed as the ratio between LD50 and ED50. Compounds and compositions exhibiting high therapeutic indices are preferred. The data obtained from cell culture assays or animal studies can be used in formulating a range of dosages for use in humans, as has long been established in the art [see, e.g., Fingl et al., in *The Pharmacological Basis of Therapeutics, Ch.* 1 p. 1(1975)].

The compounds of the present invention may be administered by a single dose, multiple discrete doses or continuous infusion. Because the compounds preferably are non-peptidic, easily diffusible and relatively stable, they can be well-suited to continuous infusion.

Dose levels on the order of about 0.1 mg to about 10,000 mg of the active ingredient are useful in the treatment of the above conditions, with preferred levels being about 0.1 mg to about 1,000 mg, and most preferably 1 mg to about 1000 mg. The specific dose level, and thus the therapeutically-effective amount, for any particular patient will vary depending upon a variety of factors, including the activity of the specific compound employed and its bioavailability at the site of drug action; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models also are helpful. The considerations for determining the proper dose levels are available to the skilled person.

In vivo test results were obtained with the 1-(2-(2-hydroxy-3-phenoxypropylamino)acetyl)pyrrolidine-2-carbonitrile hydrochloride (as shown at 7) according to the invention, which support in vivo dose levels on the order of about 0.1 mg to about 10,000, and more preferably about 0.1 mg to about 1.000 mg, and most preferably 1 mg to about 1000 mg of the active ingredient as being useful in the treatment of the above conditions. Specifically, an oral glucose tolerance test in diet-induced obese mice were conducted. Male C57BL/6 mice (6-8 weeks of age) were used. Mice were fed a lean (control group) or high-fat (DIO group) diet (5 and 35% fat by weight, respectively) for 6-9 weeks and then administered an oral glucose tolerance test. Fasted DIO mice were orally dosed with vehicle (0.5% methylcellulose) and 1-(2-(2-hydroxy-3-phenoxypropylamino)acetyl)pyrrolidine-2-carbonitrile hydrochloride (as shown at 7) at 30, 10, or 3 mg/kg, 1 hour before glucose (2 g/kg) challenge. Blood glucose was determined at various time points from tail bleeds using a glucometer. The blood glucose response curve (AUC's, $t=2$ hours) are $18.7 \pm 1.6$, $20.1 \pm 0.7$, $21.3 \pm 11.5$ for above three groups, respectively.

Suitable compounds of this invention can be administered in lyophilized form. In this case, 1 to 1000 mg, preferably 20-500 mg, of a compound of the present invention may be lyophilized in individual vials, together with a carrier and a buffer, such as mannitol and sodium phosphate. The compound may be reconstituted in the vials with bacteriostatic water before administration.

In treating a neurodegenerative disorder, for example, the compounds of the present invention are preferably administered orally, rectally, or parenterally 1 to 6 times daily, and may follow an initial bolus dose of higher concentration. In treating a cutaneous disorder, such as psoriasis or lichen planus, for example, the compounds of the present invention are preferably administered topically or orally 1-to-4 times daily.

For the compounds, methods, and uses of the present invention, any administration regimen regulating the timing and sequence of drug delivery can be used and repeated as necessary to effect treatment. Such regimen may include pretreatment and/or co-administration with additional therapeutic agents.

Additional aspects of the invention can be devised by reference to this disclosure as a whole in combination with the references cited and listed throughout and at the end of the specification and the knowledge of one skilled in the art. All of the references cited and listed can be relied on, in their entirety, to allow one to make and use these additional aspects of the invention. It should be appreciated that modifications and other embodiments may be devised by those skilled in the art. The appended claims are intended to cover all such modifications and embodiments, which would come within the spirit and scope of the present invention.

What is claimed is:

1. A dipeptidyl peptidase IV inhibiting compound of Formula II

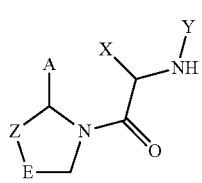

Formula II or a pharmaceutically acceptable salt thereof,
where A is selected from the group consisting of H, F or CN;
where Y is W and X is selected from the group consisting of H, W, W' or W", wherein W' is a saturated cyclic hydrocarbon, W" is a non-cyclic straight or branched chain alkyl group, and W may be a group defined by any one of Formulas III and IV

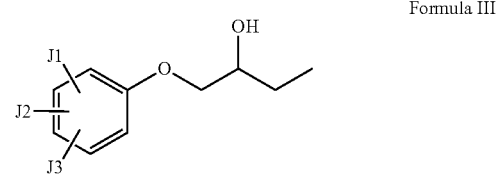

Formula III

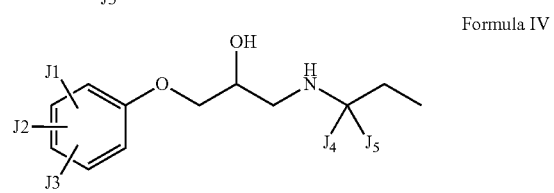

Formula IV where J1 is selected from the group consisting of hydrogen hydroxyl, hydroxymethyl, alkyl, aryl, alkoxy, and aroxy;

where J2 and J3 are independently selected from the group consisting of hydrogen, halo, hydroxy, amino, di (C1-5 alkyl) amino, mono (C1-5 alkyl) amino, nitro, cyano, C1-6 alkyl, C3-8 cycloalkyl, C2-5 alkenyl, C1-4 alkoxy, C1-4 alkylthio, C2-5 alkenyloxy, C1-5 alkanoyl, alkyl, aryl, alkoxy, and aroxy;

wherein J1 and J2 or J2 and J3 may form a cyclic ring, aliphatic or aromatic ring; and wherein J4, J5 are independently selected from the group consisting of H, F, Cl, alkyl, and aryl, where Z is selected from the group consisting of $CH_2$, $CF_2$, and CHF; and where E is any one selected from the group consisting of $CH_2$, $CF_2$ and CHF.

2. A dipeptidyl peptidase IV inhibiting compound of formula II according to claim 1 in combination with a pharmaceutically acceptable carrier, diluent, or excipient.

* * * * *